Figure 1:
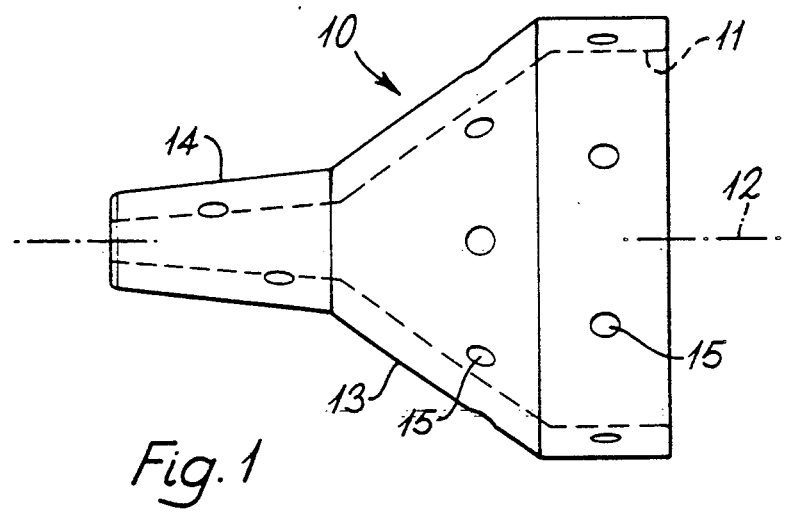

United States Patent [19]

Luesley

[11] Patent Number: 5,002,573
[45] Date of Patent: Mar. 26, 1991

[54] CERVICAL PROSTHESIS

[75] Inventor: David M. Luesley, West Midlands, England

[73] Assignee: National Research Development Corporation, London, England

[21] Appl. No.: 411,821

[22] Filed: Sep. 25, 1989

[30] Foreign Application Priority Data

Sep. 28, 1988 [GB] United Kingdom ............... 8822732

[51] Int. Cl.⁵ ................................................. A61F 2/06
[52] U.S. Cl. ....................................................... 623/12
[58] Field of Search ................... 623/1, 10, 11, 12, 16; 606/170; 604/157

[56] References Cited

U.S. PATENT DOCUMENTS

| 3,345,981 | 10/1987 | Hodges | 606/170 |
| 3,357,422 | 12/1967 | Creelman | 606/170 |
| 3,741,216 | 6/1973 | Yosowitz | |
| 3,943,916 | 3/1976 | Vadas | 606/170 |
| 4,667,684 | 5/1987 | Leigh | 604/157 |
| 4,713,074 | 12/1987 | Piacentino | 623/12 |

FOREIGN PATENT DOCUMENTS

| 87/05486 | 9/1987 | PCT Int'l Appl. | |
| 277796 | 9/1927 | United Kingdom . | |
| 684876 | 12/1952 | United Kingdom . | |

Primary Examiner—David J. Isabella
Attorney, Agent, or Firm—Cushman, Darby & Cushman

[57] ABSTRACT

A cervical prosthesis comprises a body 10 of overall generally tapered shape for securement in the cervix to support the same, but without occlusion, following cone biopsy. Preferably the wider and narrower end portions 13,14 of the body have respectively greater and lesser taper, the tapered shape is that of a surface of revolution, suitably involving conical tapering, a through passageway 11 following the direction of tapering is provided, and the body is formed with distributed transverse apertures 15.

11 Claims, 1 Drawing Sheet

CERVICAL PROSTHESIS

This invention concerns a cervical prosthesis, more particularly for use in association with cone biopsy of the uterine cervix.

This cone biopsy, or so-called conization, involves the removal of tissue from the cervix for the diagnosis and management of patients with abnormal cervical cytology, the removed tissue being cut to a conical shape generally coaxial with the cervical canal. The procedure is not without complications and these can include haemorrhage, cervical stenosis, subfertility and cervical incompetence, with stenosis occurring most commonly, in up to 40% of cases. Stenosis not only results directly in undesirable symptoms, in the form of dysmenorrhoea and amenorrhoea, but has also been found to diminish the adequacy of both cytologic and colposcopic follow-up. Reduction of the frequency with which stenosis occurs would therefore have several potential benefits and this is an object of the invention.

Conception of the invention arose from the observation, from a study of conization, that stenosis occurred less frequently with increase of apex angle and decrease of axial length in the conical shape deployed even if the area of cut tissue was at least relatively unchanged as a result, if not in fact increased. This observation led to the hypothesis that stenosis resulted from collapse of the residual cervix rather than primary fibrosis.

On the basis of this hypothesis the present invention provides a cervical prosthesis comprising a body for securement in the cervix to support the same following cone biopsy.

Such support is intended to be temporary rather than permanent, to prevent tissue collapse until healing and recovery is such as to provide an improved prospect for cervical integrity following removal of the prosthesis.

As so far developed the proposed prosthesis preferably comprises a body of overall generally tapered shape to facilitate location in the residual cervix and better support the same. This tapered shaping is conveniently that of a surface of revolution so that the body is circumferentially symmetrical and most conveniently includes a main body portion of substantially conical shape to conform with that of the cut tissue bed in the residual cervix. It is in any case preferred that the tapered shaping includes a main body portion having at its narrower end a projection of cylindrical or otherwise significantly reduced taper, such projection serving to engage in the remanent uncut endocervical canal when locating the main body portion.

Also, it is appropriate that the prosthesis should not obturate the cervix and, in this respect, the body is preferably hollowed to define a through-passageway which, when such body is tapered, extends between the narrower and broader ends of the body.

Securement of the prosthesis is conveniently by suturing and for this purpose the body is preferably formed with apertures distributed, when of tapered shape, predominantly over its wider end. Some such aperturing is preferable in any event to facilitate healing.

The prosthesis body is, of course, to be made of material which is suitably sterilisable and biocompatible and has appropriate physical properties for the intended usage. In these respects it is presently preferred that the body be made in one piece of an autoclavable high density plastics material.

Figure 2:
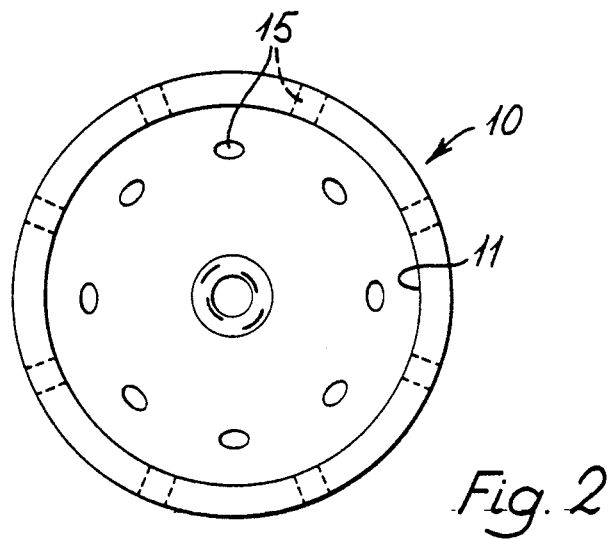

In order to clarify the invention further one specific embodiment thereof is described below, by way of example, with reference to the accompanying drawings, in which:

FIGS. 1 and 2 diagrammatically illustrate the relevant prosthesis respectively in side and end views, with the latter view being taken from the right hand, wider end of the former.

The illustrated prosthesis comprises a body 10 of overall tapered shape hollowed to define a through-passageway 11 extending between its wider and narrower ends. The body 10 is of one-piece construction and is made of ultra high molecular weight polyethylene.

The overall tapered shape is formed as a surface of revolution about an axis 12. This surface commences from the wider end of the body to bound a main body portion 13 which is first cylindrical over a minor axial length and then conical. Thereafter the surface bounds an axial projection 14 from the narrower end of the main body portion, which projection is of significantly reduced taper.

The passageway 11 follows similar shape to that of the body exterior so that the body is of relatively uniform wall thickness.

The remaining feature of the body is the provision of a plurality of apertures 15. These apertures are distributed over the body, but predominantly towards the wider end, with a uniformly spaced row around the cylindrical part of the main body portion, a further such row around the adjoining conical part but in circumferentially off-set relation, and a few along and around the projection.

In this embodiment as designed for initial trial of the invention, the main body portion has a cylindrical part of 20 mm diameter and 6 mm length and a conical part tapering to a diameter of 7 mm at an inclination of about 35° over a length of 9 mm, while the projection extends over a length of 10 mm and tapers at an inclination of about 5° to a diameter of about 5 mm. The body wall thickness is 1.5 mm and the apertures have a diameter of 1 mm, with 8 apertures in each row at the wider end and 2 pairs of diametrally opposed apertures along the projection.

The prosthesis is located in use after cone biopsy which typically involves tissue removal by cold knife, followed by placement of two lateral cervical sutures to ligate the descending branches of the uterine arteries. These sutures do not impinge on the cut tissue surface of the residual cervix. Further haemostasis is achieved by diathermy to small vessels on the cut tissue surface.

The prosthesis is then located with its projection engaged in the endocervical canal until the wider end seats against the cut tissue surface. When located, the prosthesis is secured by a number of sutures, say four, placed uniformly around the cervix and passing through adjacent apertures in the prosthesis to anchor the latter. The prosthesis can be removed after a suitable period of about two weeks simply by lifting out after cutting the retaining sutures. Cytologic and colposcopic follow-up is performed after a further suitable period of about four months.

While the invention has been described with reference to the illustrated embodiment, it is not intended to be limited thereby as is evident from the more general introductory discussion of the invention and viable variations from the embodiment will be obvious to those skilled in the art on the basis of such introduction. For example the body may be made of a porous rather than solid material although, even then, the provision of a bore to ensure non-occlusion and apertures for association with sutures may still be appropriate.

I claim:

1. A cervical prosthesis comprising:
   a non-occlusive body dimensioned for securement in the cervix to support the same following surgical conization, said body has an outer surface having an overall progressively taper from a wider end portion to a narrower end portion along the length thereof, said narrower end portion having a significantly lesser taper than said wider end portion.

2. A prosthesis according to claim 1 wherein said outer surface is that of a surface of revolution.

3. A prosthesis according to claim 2 wherein said outer surface includes at least one conical portion.

4. A prosthesis according to claim 1 wherein said body has a passageway extending along the length thereof.

5. A prosthesis according to claim 4 wherein said body has substantially uniform wall thickness about said passageway.

6. A prosthesis according to claim 4 wherein said body is formed with a plurality of apertures extending therethrough transversely of said passageway and distributed circumferentially therearound over at least the wider end portion of said tapered shape.

7. A prosthesis according to claim 1 wherein said body is made of porous material.

8. A prosthesis according to claim 1 wherein said body is made of plastics material.

9. A cervical implant consisting essentially of:
   an implant body dimensioned for securement in the cervix to support the same following surgical conization, said body having a longitudinal axis, a first substantially cylindrical end portion, a second tapered end portion and a progressively tapered mid-portion extending between and interconnecting said first end portion and said second end portion, the taper of said second end portion being substantially less than a taper of said mid-portion;
   a flow passage defined through said implant body along said longitudinal axis from said first end to said second end; and
   a plurality of apertures defined through said implant body transversely of said flow passage.

10. A prosthesis according to claim 9, wherein said apertures are defined circumferentially about said implant body.

11. A prosthesis according to claim 9, wherein said apertures extend through at least said first end portion of said implant body.

* * * * *